(12) United States Patent
Bachmann

(10) Patent No.: US 9,745,245 B2
(45) Date of Patent: Aug. 29, 2017

(54) ALPHA-BRANCHED ALKENOIC ACIDS AND THE USE OF ALPHA-BRANCHED ALKANOIC AND ALKENOIC ACIDS AS A FRAGRANCE

(75) Inventor: Jean-Pierre Bachmann, Wädenswil (CH)

(73) Assignee: Givaudan S.A., Vernier (CH)

( * ) Notice: Subject to any disclaimer, the term of this patent is extended or adjusted under 35 U.S.C. 154(b) by 486 days.

(21) Appl. No.: 13/130,847

(22) PCT Filed: Dec. 2, 2009

(86) PCT No.: PCT/CH2009/000385
§ 371 (c)(1),
(2), (4) Date: May 24, 2011

(87) PCT Pub. No.: WO2010/063133
PCT Pub. Date: Jun. 10, 2010

(65) Prior Publication Data
US 2011/0263725 A1    Oct. 27, 2011

(30) Foreign Application Priority Data
Dec. 3, 2008  (GB) .................................. 0822091.5

(51) Int. Cl.
*A61Q 13/00*     (2006.01)
*C07C 53/128*    (2006.01)
*C07C 57/03*     (2006.01)

(52) U.S. Cl.
CPC ............ *C07C 53/128* (2013.01); *A61Q 13/00* (2013.01); *C07C 57/03* (2013.01)

(58) Field of Classification Search
CPC ........ C07C 53/128; C07C 57/03; A61Q 13/00
See application file for complete search history.

(56) References Cited

U.S. PATENT DOCUMENTS

| 5,726,141 A * | 3/1998 | Ofosu-Asante ............... 510/220 |
| 2003/0078179 A1 * | 4/2003 | Ghosh et al. ................. 510/392 |
| 2005/0153869 A1 | 7/2005 | Connor et al. |

FOREIGN PATENT DOCUMENTS

| GB | 2 142 632 A | 1/1985 |
| JP | 2003-327557 | 11/2003 |
| JP | 2006 124490 A | 5/2006 |
| WO | WO 2004/087632 A1 | 10/2004 |
| WO | WO 2007/033508 A2 | 3/2007 |

OTHER PUBLICATIONS

PCT/CH2009/000385—Written Opinion of the International Searching Authority, Jan. 21, 2010.
PCT/CH2009/000385—International Search Report, Jan. 21, 2010.
GB 0822091.3—Great Britain Search Report, Mar. 20, 2009.
"Part II: Allergenicity of synthetic alkane-α,β-diols and alkane α,ω-diols". Journal of the Society of Cosmetic Chemist ,1983, vol. 34, No. 2, pp. 115-125.
Baán, Gabor, et al., "Efficient Synthesis of the Components of the German Cockroach Sex Peromone I", Croatica Chemica Acta, 1986, vol. 59, No. 1, pp. 177-181.
De-Sheng Ding, et al., "Studies on the Volatile Components of Secretion From Chinese Civet", Developments in Food Science, Flavors and Fragrances, 1988, vol. 18, pp. 587-600.
J.K. Ha, et al., "Volatile Branched-chain Fatty Acids and Phenolic Compounds in Aged Italian Cheese Flavors", Journal of Food Science, 1991, vol. 56, No. 5, pp. 1241-1247, XP-002562173.
Japanese Office Action for corresponding foreign application—mailing date Apr. 1, 2014.

* cited by examiner

*Primary Examiner* — Theodore R West
(74) *Attorney, Agent, or Firm* — Curatolo Sidoti Co., LPA; Joseph G. Curatolo; Salvatore A. Sidoti

(57) ABSTRACT

The present invention refers to alpha branched alkanoic and alkenoic acids of formula (I)

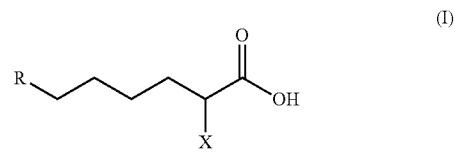

(I)

wherein X and R have the same meaning as given in the description.
The invention further refers to perfume compositions and fragrance applications comprising them.

5 Claims, No Drawings

ALPHA-BRANCHED ALKENOIC ACIDS AND THE USE OF ALPHA-BRANCHED ALKANOIC AND ALKENOIC ACIDS AS A FRAGRANCE

CROSS REFERENCE TO RELATED APPLICATIONS

This application is a national stage application of International Application No. PCT/CH2009/000385, filed 2 Dec. 2009, which claims priority from Great Britain Patent Application Serial No. 0822091.2, filed 3 Dec. 2008, from which applications priority is claimed, and which are incorporated herein by reference.

The present invention refers to alpha branched alkanoic and alkenoic acids and their use as odorants. This invention relates furthermore to a method of their production and fragrance compositions comprising them.

In the fragrance industry there is a constant demand for new compounds that enhance, modify or improve on odour notes. Surprisingly, it has now been found that alpha branched alkanoic and alkenoic acids of formula (I) as defined below constitute very powerful olibanum, citrus odorants whereas the corresponding carboxylic acids without the substituent X are described possessing a fatty, waxy, sour and acidic odour note.

Accordingly, the present invention refers in one of its aspects to the use as fragrance of a compound of formula (I)

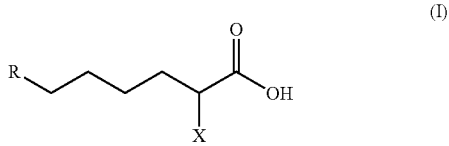

(I)

wherein
X is selected from methyl and ethyl;
R is selected from $C_4$-$C_6$ alkyl (e.g. pentyl), and $C_4$-$C_6$ alkenyl (e.g. but-2-enyl, but-3-enyl, pentenyl such as pent-3-enyl, pent-4-enyl, and hex-4-enyl).

The compounds of formula (I) may comprise one or several chiral centres or E- or Z-configured double bonds and as such may exist as a mixture of stereoisomers, or they may be resolved into isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Non-limiting examples are compound of formula (I) wherein X is methyl and R is linear $C_4$-$C_6$ alkyl, and compounds of formula (I) wherein X is ethyl and R is linear $C_4$-$C_6$ alkyl.

Further, non-limiting examples are compounds of formula (I) wherein X is methyl and R is linear $C_4$-$C_6$ alkenyl, and compounds of formula (I) wherein X is ethyl and R is linear $C_4$-$C_6$ alkenyl.

In particular embodiments are compounds of formula (I) selected from the list consisting of 2-methyl decanoic acid, 2-methyl undecanoic acid, 2-ethyl decanoic acid, 2-ethyl undecanoic acid, 2-methyl undec-9-enoic acid, 2-methyl undec-10-enoic acid, 2-methyl undec-8-enoic acid, 2-methyl undec-7-enoic acid and 2-methyl dodecanoic acid.

Amongst the compounds of formula (I), one may cite 2-methyl undecanoic acid, which is one of the most appreciated by the perfumer. This compound possess a very powerful and diffusive note of aldehyde and natural resins mainly olibnum and myrrh combined with a sparkling elemi dimension and orris and ambrette seed background. This compound possess all the odor attributes linked to a natural frankincense which however needs burning for developing the typical fragrance note.

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a base material, e.g. a diluent conventionally used in conjunction with odorants, such as dipropyleneglycol (DPG), isopropylmyristate (IPM), triethylcitrate (TEC) and alcohol (e.g. ethanol).

The following list comprises examples of known odorant molecules, which may be combined with the compounds of the present invention:
essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;
alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;
aldehydes and ketones, e.g. anisaldehyde, α-amylcinnamaldehyde, Georgywood™, hydroxycitronellal, Iso E® Super, Isoraldeine®, Hedione®, Lilial®, maltol, Methyl cedryl ketone, methylionone, verbenone or vanillin;
ethers and acetals, e.g. Ambrox™, geranyl methyl ether, rose oxide or Spirambrene™;
esters and lactones, e.g. benzyl acetate, Cedryl acetate, γ-decalactone, Helvetolide®, γ-undecalactone or Vetivenyl acetate;
macrocycles, e.g. Ambrettolide, Ethylene brassylate or Exaltolide®;
heterocycles, e.g. isobutylquinoline.

The compounds according to formula (I) may be used in a broad range of fragrance applications, e.g. in any field of fine and functional perfumery, such as perfumes, air care products, household products, laundry products, body care products and cosmetics. Further examples of fine perfumery are Eau de perfume, Eau de Toilette, Eau de Cologne and Splash Cologne. Fine perfumery products are commonly based on an alcoholic solution as diluent. However fine perfumery products using an oil or wax as diluent may also be included within the meaning of this invention. The compounds can be employed in widely varying amounts, depending upon the specific application and on the nature and quantity of other odourant ingredients. The proportion is typically from 0.0001 to 10 weight percent of the application. In one embodiment, compounds of the present invention may be employed in a fabric softener in an amount of from 0.0001 to 0.04 weight percent. In another embodiment, compounds of the present invention may be used in fine perfumery in amounts of from 0.01 to 10 weight percent, more preferably between 0.01 and 5 weight percent, e.g. up to 2 weight percent. However, these values are given only by way of example, since the experienced perfumer may also achieve effects or may create novel accords with lower or higher concentrations.

The compounds as described hereinabove may be employed in a consumer product base simply by directly mixing the compound of formula (I), a mixture thereof, or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a fragrance application, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of a compound of the present invention as hereinabove described, or a mixture thereof, the odour notes of a consumer product base will be improved, enhanced or modified.

Thus, the invention furthermore provides a method for improving, enhancing or modifying a consumer product base by means of the addition thereto of an olfactorily acceptable amount of a compound of formula (I), or a mixture thereof.

The invention also provides a fragrance application comprising:
  a) as odorant a compound of formula (I), or a mixture thereof; and
  b) a consumer product base; and
  c) optionally a further odorant molecule.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

The compounds of formula (I) may be prepared from the corresponding aldehydes by oxidation methods known to the person skilled in the art of organic synthesis.

The invention is now further described with reference to the following non-limiting examples. These examples are for the purpose of illustration only and it is understood that variations and modifications can be made by one skilled in the art.

The reported NMR spectra were measured in CDCl$_3$ if not otherwise stated; chemical shifts (δ) are reported in ppm downfield from TMS; coupling constants J in Hz.

Flash chromatography: Merck silica gel 60 (230-400 mesh).

EXAMPLE 1

2-methylundecanoic acid

Jones reagent (61 ml, containing 163 mmol CrO$_3$ and 280 mmol H$_2$SO$_4$) was added dropwise to the cooled (−25° C.) solution of 2-methylundecanal (45.0 g, 245 mmol) in acetone (80 ml) during 20 min. The solution was stirred at −5° C. for further 15 min, then poured into a biphasic mixture of 10% aq. NaOH-solution (400 g) and toluene (400 ml) and thoroughly stirred for 15 min. The phases were separated in a separatory funnel (emulsions were broken by the addition of small amounts of EtOH and solid NaCl). The alkaline aqueous layer was transferred into an Erlenmeyer flask, mixed with toluene (ca. 100 ml), and acidified by the addition of 6 N aqueous HCl-solution (200 ml, 1.2 mol). The aqueous layer is then extracted with toluene, washed neutral with half-saturated aq. NaCl-solution and dried over MgSO$_4$. After removal of the solvent, the crude was subjected to a short-path distillation at 0.05 mbar/111-123° C., followed by fine distillation over a Vigreux-column at 0.05 mbar/118-121° C. to yield 20.1 g (41%) of 2-methylundecanoic acid as a colourless oil.

IR (thin film): 2923m, 2854m, 1703vs, 1465w, 1236w, 938w., $^1$H-NMR (400 MHz, CDCl$_3$): 11.76 (br. s, 1 H); 2.44 (hex, J=7.0 Hz, 1 H); 1.71-1.63 (m, 1 H); 1.46-1.37 (m, 1 H); 1.35-1.23 (m, 14 H); 1.16 (d, J=6.8 Hz, 3 H); 0.87 (t, J=7.0 Hz, 3 H).

$^{13}$C-NMR (100 MHz, CDCl$_3$): 183.7 (s), 39.4 (d), 33.5 (t), 31.9 (t), 29.6 (t), 29.5 (t), 29.5 (t), 29.3 (t), 27.1 (t), 22.7 (t), 16.8 (q), 14.1 (q).

MS (EI, 70 eV): 200 (2, M$^+$), 185 (<1), 171 (1), 157 (5), 143 (11), 129 (7), 87 (41), 74 (100).

Odour description: Olibanum, Elemi, citrus

EXAMPLE 2

2-Methyldecanoic acid

Following the protocol according to Example 1, 2-methyldecanoic acid was prepared starting from 2-methyldecanal. The title compound was purified by fine distillation over a Vigreux-column at 0.05 mbar/115-130° C. (colourless oil, yield 49%).

IR (thin film): 2924m, 2855m, 1703vs, 1465w, 1238w, 938w.

$^1$H-NMR (400 MHz, CDCl$_3$): 11.59 (br. s, 1 H); 2.44 (hex, J=6.9 Hz, 1 H); 1.73-1.62 (m, 1 H); 1.47-1.37 (m, 1 H); 1.36-1.22 (m, 12 H); 1.16 (d, J=6.8 Hz, 3 H); 0.87 (t, J=7.0 Hz, 3 H).

$^{13}$C-NMR (100 MHz, CDCl$_3$): 183.5 (s), 39.4 (d), 33.5 (t), 31.9 (t), 29.5 (t), 29.4 (t), 29.2 (t), 27.1 (t), 22.7 (t), 16.8 (q), 14.1 (q).

MS (EI, 70 eV): 186 (2, M$^+$), 143 (9), 129 (11), 87 (39), 74 (100), 55 (20).

Odour description: citrus, aldehydic, resinous, Olibanum.

EXAMPLE 3

2-Methyl dodecanoic acid

Following the protocol according to Example 1, 2-methyldodecanoic acid may be prepared starting from 2-methyldodecanal.

Odour description: aldehydic, resinous, raspberry.

EXAMPLE 4

Further Compounds

The following compounds may be prepared following the protocol according to Example 1: 2-ethyl decanoic acid; 2-ethyl undecanoic acid; 2-methyl undec-9-enoic acid; and 2-methyl undec-10-enoic acid;

EXAMPLE 5

2-Methyl undec-9-enoic acid and 2-methyl undec-10-enoic acid a) Sulfuric acid (62%, 88.7 g, 0.56 mol, 1.1 equiv.) is added at 10° C. to diethylamine (81.4 g, 1.1 mol, 1.1 equiv.) Formaldehyde (36.5% in water, 93.3 g, 1.12 mol, 1.12 equiv.) is added to the white suspension at 15° C. At the same temperature are added dropwise over 25 min the solution of BHT (0.67 g) in aldehyde iso C11 (mixture of E-/Z-9-undecenal and 10-undecenal; 168 g, 1 mol). The mixture was further stirred during 1.5 h at room temperature, during 3.5 h at 110° C. and during 16 h at room temperature. The mixture was diluted with cyclohexane and the organic layer washed 3 times with water, once with sat. aq. $NaHCO_3$ and twice with brine. The crude obtained after drying the organic layer with $MgSO_4$ and removing the solvents was pre-purified by a short-path distillation at 0.06 mbar/90° C. to isolate 119 g (66%) of a colourless oil, which was fine-distilled at 0.05 mbar/71-79° C. to isolate 104 g (58%) of a mixture of 2-methylene undec-9-enal (1) and 2-methylene undec-10-enal (2) as a colourless oil.

$^1$H-NMR (400 MHz, $CDCl_3$): 9.54 (s, 1H), 6.24 (s, 1H), 5.98 (s, 1H), 5.85-5.75 (m, 0.14H), 5.43-5.31 (m, 1.6H), 4.99-4.88 (m, 0.29H), 2.23 (t, J=7.6, 2H), 2.03-1.90 (m, 2H), 1.62-1.56 (m, 2H), 1.45-1.39 (m, 3H), 1.35-1.23 (m, 8H).

MS (EI, 70 eV): (1) 180 ($M^+$, 2), 165 (2), 151 (8), 123 (9), 109 (17), 95 (29), 81 (33), 67 (41), 55 (100).

b) The mixture of 2-methylene undec-9-enal (1) and 2-methylene undec-10-enal (2) (18 g, 100 mmol) prepared above was treated with triethylsilane (12.2 g, 105 mmol, 1.05 equiv.) and tris(triphenylphosphine)chlororhodium(I) (100 mg, 0.1 mmol, 0.1 mol-%) and the resulting solution stirred at 50° C. for 1 h and at 60° C. for 2 h. The dark mixture was diluted with hexane and the solution washed 3 times with water. After drying the organic layer over $MgSO_4$ and removal of the solvent a yellow oil was obtained (30.1 g), which was distilled at 0.06 mbar/105-133° C. to yield a colourless oil (20.8 g, 70%). This product (15 g, 50.6 mmol) was dissolved in toluene (50 ml). The solution was cooled to 5° C. and a solution of tetrabutyl ammonium fluoride (1 M in THF, 20 ml, 20 mmol, 0.4 equiv.) was added dropwise over 4 min, followed by the addition of solid potassium fluoride (5.8 g, 100 mmol, 2 equiv) and methanol (50 ml). The resulting white suspension was stirred at 0-5° C. for 3 h, then treated with sat. aq. $NaHCO_3$ solution (80 ml) and stirred thoroughly for 15 min. The mixture was extracted with methyl t-butyl ether and the organic layer washed 3 times with brine/water 1:1. The organic layer was dried over $MgSO_4$ and the solvent removed. The resulting colourless oil (15 g) was purified by flash column chromatography over silica gel with hexane/toluene 1:1 to yield 5.74 g (31%) of a colourless oil, which was further purified by distillation at 0.05 mbar/58-62° C. to yield 2.2 g (7%) of a colourless oil. Of this product, 1.09 g (6 mmol) were dissolved in ethanol (20 ml) and a solution of silver nitrate (2.24 g, 13.2 mmol, 2.2 equiv.) in water (10 ml) was added, followed by a 12.5% wt/wt aqueous sodium hydroxide solution (30 g, 94 mmol). During the addition, the temperature rose to 35° C. The grey emulsion was stirred intensely for 22 h at room temperature. The precipitate was removed by filtration and the filter cake was rinsed thoroughly with ethanol. The ethanol was removed from the filtrate and the residual alkaline aqueous solution was diluted with methyl t-butyl ether. The aqueous phase was separated and the organic layer was extracted with 4 N aq. NaOH. The combined alkaline aqueous layers were washed with methyl t-butyl ether, then acidified with dilute hydrochloric acid to pH 1 and extracted with methyl t-butyl ether. The organic layer was washed with brine, dried over $MgSO_4$ and concentrated in the rotary evaporator. The residue was purified by bulb-to-bulb distillation at 0.06 mbar/140-150° C. to isolate 1.15 g (96%) of colourless oil, which consisted of a mixture of E-2-methylundec-9-enoic acid (3a, 56.3%), Z-2-methylundec-9-enoic acid (3b, 32.4%) and 2-methylundec-10-enoic acid (4, 11.3%).

IR (thin film): 3500-2600 br, 2925 m, 2855 w, 1703 vs.

$^1$H-NMR (400 MHz, $CDCl_3$): δ ppm 11.8 (br. s, 1H), 5.80 (m, 0.2H), 5.39 (m, 1.8H), 4.94 (m, 0.4H), 2.44 (td, J=13.8, 6.9 Hz, 1H), 1.99 (m, 2H), 1.64 (m, 3H), 1.36 (m, 10H), 1.16 (d, J=6.7 Hz, 3H).

MS (EI, 70 eV): (3a) 198 ($M^+$, 4), 180 (5), 165 (<1), 125 (11), 87 (32), 74 (89), 69 (65), 55 (100).

(3b) 198 ($M^+$, 4), 180 (7), 165 (<1), 125 (13), 87 (30), 74 (91), 55 (100).

(4) 198 ($M^+$, 2), 180 (5), 165 (<1), 125 (9), 87 (24), 74 (100).

Odour description: incense, olibanum.

EXAMPLE 6

Further Compounds

The following compounds may be prepared following the protocol according to Example 5: 2-methyl undec-8-enoic acid and 2-methyl undec-7-enoic acid.

EXAMPLE 7

Preparation of Perfume Accords

Base Accord:

| Ingredients | Weight parts |
|---|---|
| Cashmeran 10% in Diethylphtalate (6,7-dihydro-1,1,2,3,3-pentamethyl-4(5H)-indanone) | 8 |
| Frankincense 50% in Diisopropylphtalate | 8 |
| Ethyl Vanillin 0.1% in Dipropylene glycol | 1 |
| Georgywood * (1-(1,2,3,4,5,6,7,8-octahydro-1,2,8,8-tetramethyl-2-naphthalenyl)ethanone) | 10 |
| Hedione (methyl (2-pentyl-3-oxocyclopentyl)acetate) | 20 |
| Javanol* 10% in dipropylene glycol ((1-methyl-2-((1,2,2-trimethylbicyclo[3.1.0]hexan-3-yl)methyl)cyclopropyl)methanol) | 8 |
| Phenoxanol (3-methyl-5-phenylpentan-1-ol) | 16 |
| Moxalone* 50% in triethyl citrate (1a,2,3,4,5,6,7,7a-octahydro-1a,3,3,4,6,6-hexamethyl-naphth[2,3-b]oxirene) | 9 |
| Pepperwood* (dimethylcarbamic acid 3,7-dimethylocta-1,6-dien-3-yl ester) | 16 |
| Dipropylene glycol | 4 |
| Total: | 100 |

*Givaudan Schweiz AG, Vernier 5.1: The replacement of 4% of dipropylene glycol in the above base accord formula by 4% of 2-methyldecanoic acid at 10% in dipropylene glycol brings a fresh, sparkling, natural, citrus note and a rich natural woody piney note, characteristic of fir.

5.2: The replacement of 4% of dipropylene glycol in the above base accord formula by 2-methylundecanoic acid at 10% in dipropylene glycol imparts an intense, rich and natural olibanum note, characteristic of burning olibanum.

The invention claimed is:

1. A fine perfumery comprising as odorant a compound of formula (I) or a mixture thereof,

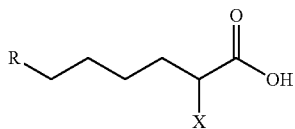

(I)

wherein

X is selected from methyl and ethyl;

R is selected from $C_4$-$C_6$ alkyl and $C_4$-$C_6$ alkenyl, and a fine perfumery consumer product base, and wherein the fine perfumery comprises an olfactory acceptable amount up to 2 weight % of the odorant compound of formula (I) or a mixture thereof.

2. The fine perfumery according to claim 1 wherein the compound of formula (I) is selected from the group consisting of 2-methyl decanoic acid, 2-methyl undecanoic acid, 2-ethyl decanoic acid, 2-ethyl undecanoic acid, 2-methyl undec-9-enoic acid, 2-methyl undec-10-enoic acid, 2-methyl undec-8-enoic acid, 2-methyl undec-7-enoic acid and 2-methyl dodecanoic acid.

3. The fine perfumery according to claim 1 wherein the compound of formula (I) comprises 2-methyl undecanoic acid.

4. A method of improving, enhancing or modifying a consumer product base comprising adding to the consumer product base as odorant an olfactory acceptable amount of a compound of formula (I) or a mixture thereof

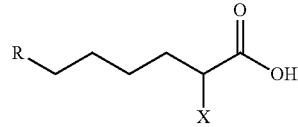

(I)

wherein

X is selected from methyl and ethyl;

R is selected from $C_4$-$C_6$ alkyl and $C_4$-$C_6$ alkenyl, wherein the olfactory acceptable amount comprises up to 2 weight % of a compound of formula (I) or a mixture thereof, wherein the consumer product base is a fine perfumery.

5. The method according to claim 4 wherein the compound of formula (I) is selected from the group consisting of 2-methyl decanoic acid, 2-methyl undecanoic acid, 2-ethyl decanoic acid, 2-ethyl undecanoic acid, 2-methyl undec-9-enoic acid, 2-methyl undec-10-enoic acid, 2-methyl undec-8-enoic acid, 2-methyl undec-7-enoic acid and 2-methyl dodecanoic acid.

* * * * *